(12) United States Patent
Paul et al.

(10) Patent No.: US 6,274,758 B1
(45) Date of Patent: Aug. 14, 2001

(54) ASYMMETRIC HYDROGENATION OF VINYL SULFONES

(75) Inventors: Jane Marie Paul; Christopher Palmer, both of Cambridge (GB)

(73) Assignee: Darwin Discovery, Ltd. (GB)

( * ) Notice: Subject to any disclaimer, the term of this patent is extended or adjusted under 35 U.S.C. 154(b) by 0 days.

(21) Appl. No.: 09/159,920

(22) Filed: Sep. 24, 1998

(30) Foreign Application Priority Data

Sep. 24, 1997 (GB) ................................. 9720351
Mar. 24, 1998 (GB) ................................. 9806284

(51) Int. Cl.$^7$ ................................. C07C 315/04
(52) U.S. Cl. ................ 560/150; 562/512; 568/28; 568/30; 568/31; 564/123
(58) Field of Search ................ 568/28, 30, 31; 560/150; 562/512; 548/319.1; 546/314; 564/123

(56) References Cited

U.S. PATENT DOCUMENTS 3,489,786 * 1/1970 Dewhirst ........................ 585/467
5,008,547 * 4/1991 Molteni ........................ 250/368

OTHER PUBLICATIONS

CA: 122:55724 abs of JP06172300, Dec. 1992.*
CA:128 : 75188 abs of WO9749679, Jun. 1997.*
Ando, D., C. Bevan, J. Brown, D. Price (1992) "Contrasting Pathways for the Directed Homogeneous Hydrogenation of Vinyl Sulfoxides and Vinyl Sulfones" J. Chem. Soc. Chem. Commun. pp 592–594.

Heiner, J. (1994) "Asymmetric C=C—Hydrogenation of a Substrate with Sulfur Functionality, Influence of Solvent and Substrate Configuration on Enantioselectivity." Tetrahedron Asymmetry 5(5):1183–1186.

* cited by examiner

*Primary Examiner*—Jean F Vollano
(74) *Attorney, Agent, or Firm*—Saliwanchik, Lloyd & Saliwanchik

(57) ABSTRACT

A process for the preparation of an enantioenriched sulfone of formula (1), which comprises asymmetric hydrogenation of vinyl sulfone of formula (2)

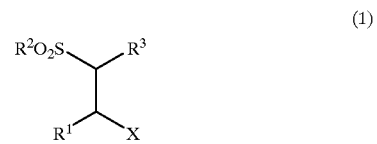

(1)

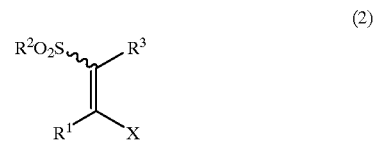

(2)

wherein $R^1$ and $R^2$ are each independently a hydrocarbon group of less than 20 carbons atoms, optionally substituted at any position, or either of $R^1$ and $R^3$ is H, and X is a coordinating group, in the presence of a stereoselective chiral catalyst.

14 Claims, No Drawings

ASYMMETRIC HYDROGENATION OF VINYL SULFONES

FIELD OF THE INVENTION

This invention relates to the preparation of enantiomerically enriched sulfones via asymmetric hydrogenation of vinyl sulfones.

BACKGROUND OF THE INVENTION

Enantipure sulfones, e.g. of the formula $R^1$—CHX—$CHR^3$—$SO_2R^2$ (1), are of interest as synthetic building blocks, for example, as intermediates in the preparation of enantiopure hydroxamic acids which are under investigation as MMP inhibitors, as described in, inter alia, WO-A-9805635. The enantiopure hydroxamic acids may be prepared by resolution of an intermediate; however, resolution processes are inefficient, with a maximum yield 50% of the correct enantiomer being obtainable. For drug manufacture, an asymmetric synthesis which provides a single enantiomer is often more attractive.

3-Substituted 2-sulfonylmethylpropionic acids have been prepared in moderate e.e. (enantiomeric excess), i.e. up to around 80% e.e. in two steps, from the corresponding allyl sulfides, by sequential asymmetric hydrogenation and oxidation at sulfur (DE-A-4233100; Jendralla, Tetrahedron: Asymmetry (1994) 5:1183–1186; Beck et al, Tetrahedron (1994) 50:4691–4698; Jendrella, Proceedings of Chira Tech '97 (The Catalyst Group). The requisite allyl sulfides are normally prepared as E/Z mixtures by a Wittig olefination reaction; subsequent separation of geometric isomers is required to give optimum results in the asymmetric hydrogenation process. For example, (E)-2-tert-butylthiomethyl-3-(1-naphthyl)acrylic acid was hydrogenated in methanol using a catalyst prepared from (S)-(−)-BINAP, benzeneruthenium (II) chloride dimer and NaOAc at 150° C. and 13800 kPa (2000 psi), followed by peracid oxidation to give (S)-3-tert-butylsulfonyl-2-(1-naphthylmethyl)propionic acid. Similar results were achieved via hydrogenation of the corresponding cyclohexylamine salt form. To access (S)-3-tert-butylsulfonyl-2-(1-naphthylmethyl)propionic acid in >99% e.e. required additional processing, with concomitant loss of yield, by crystallisation of diastereomeric salts formed with (R)-1-phenylethylamine.

Homogeneous diastereoselective hydrogenation of (α-hydroxyalkyl)vinyl sulfones of formula 3

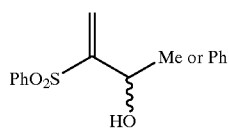

(3)

with an achiral Rh catalyst is known (Ando el al, J. Chem. Soc., Chem. Commun. (1992) 592), giving hydrogenated material in high d.e. This reaction was elaborated by carrying out a kinetic resolution of an (α-hydroxyalkyl)vinyl sulfone using (S,S)-dipamp Rh. The starting (α-hydroxyalkyl)vinyl sulfone was recovered in 76% e.e. at 50% substrate conversion and 89% e.e. at 57% conversion. The authors indicated that diasteroselectivity is controlled predominantly by coordination of the catalyst to the α-OH group at the chiral center of the substrated. However, the products have limited utility as synthetic intermediates.

This directing group effect may be akin to that required in asymmetric hydrogenation of other substrate classes. For example, the preparation of α-amino acids by asymmetric hydrogenation of enamides requires a group such as acetyl (Ac) on the nitrogen, which then has to be removed carefully under conditions giving minimal racemisation at the newly created chiral centre.

SUMMARY OF THE INVENTION

This invention is based on the surprising discovery that prochiral vinyl sulphones of formula (2) can be hydrogenated with high enantioselectivity, in the presence of a chiral catalyst, to give enantioenriched or enantiopure sulfones of formula (1)

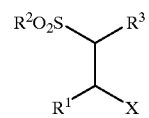

(1)

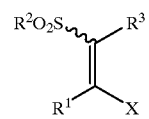

(2)

By contrast to the disclosure of Ando et al, no OH group is required as a directing group in the β-position with respect to the sulfone (i.e. as in compound (3) above); the vinyl sulfones (2) are prochiral. The reaction does not require elevated temperature or pressure to achieve good chemical conversion and high enanthioselectivity. Typically, this hydrogenation can be carried out at low to moderate pressure, e.g. 7–4140 kPa (1–600 psi) and low temperatures, e.g. 0 to 60° C.

The desired sulfone product (1) is produced directly, without the need for subsequent oxidation at sulfur. In addition, the coordinating group X present in (1) provides versatile functionality for further synthetic transformations, e.g. to prepare biologically active compounds such as those described in WO-A-9805635. The sulfone group itself also facilitates a wide range of reactions, such as those reviewed by Simpkins "Sulfones in Organic Synthesis", pub. Pergamon (1993). The process of the subject invention may additionally comprise converting the group X to give an enantiopure compound having therapeutic utility as an inhibitior of matrix metalloproteinases.

DESCRIPTION OF THE INVENTION

In formulae (1) and (2): $R^1$, $R^2$ and $R^3$ are each any hydrocarbon group of less than 20 carbon atoms, optionally substituted at any position; in addition, either of $R^1$ and $R^3$ may be H. The nature of any substituent is not critical to the generality of the procedure.

X will not normally be removable; it is a co-ordinating group including, but not restricted to, $CO_2H$ or a salt form thereof, $CO_2R$, CONHOH, $CONH_2$, CONHR, $CONR_2$ etc. The substrate (1) for hydrogenation may be in the form of a single geometric isomer, e.g. E, wherein $R^2SO_2$ and X groups are trans. However, this is not always necessary, since certain hydrogenation catalysts allow the enantioconvergent reaction of E/Z mixtures.

The complex which comprises the hydrogenation catalyst is made up of a transition metal, preferably rhodium, ruthenium or iridium, and a chiral ligand, preferably mono or diphosphines. Rhodium is especially preferred as the metal.

Cyclic phosphines are preferred, especially those incorporating a trans-2,5-disubstituted phospholane moiety (4)

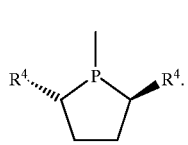

(4)

or its antipode, wherein $R^4$ is a hydrocarbon substituent of up to 20 C atoms, typically $C_{1-10}$ linear or branched alkyl. Known examples of such phosphines are those in the DuPHOS (U.S. Pat. No. 5,171,892) and BPE (U.S. Pat. No. 5,008,457) series. Known examples of the catalysts include [(S,S)-EtDuPHOS Rh (COD)]$BF_4$, [(R,R)-MeDuPHOS Rh (COD)]$BF_4$, [(S,S)-iPrDuPHOS Rh (COD)]$BF_4$, and [(R,R)-MeBPE Rh (COD)]$BF_4$. Both enantiomers of these catalysts are available with equal facility, and therefore either enantiomer of the sulphone (2) can be obtained by the asymmetric hydrogenation.

Alternative catalyst complexes, of the phosphetane type, are described in WO-A-9802445.

In a preferred embodiment of the present invention, vinyl sulfone (2a) [2: $R^1$ is Pr, $R^2$ is 4-o-methoxybenzyl, $R^3$ is H and X is $CO_2H$] was hydrogenated using [(S,S)-EtDuPHOS Rh (COD)]$BF_4$ in methanol at 1035 kPa (150 psi) hydrogen at room temperature for 2 hours, after which time complete substrate conversion was observed. Chiral HPLC showed that the hydrogenated sulfone (1a) [variable defined as for 2a] had an e.e. of 96%. Asymmetric hydrogenation of analogues of (2a), bearing additional functionality in the $R^1$ substituent, was similarly successful.

The vinyl sulfones (starting materials) for the process of the invention may be conveniently prepared using a modified version of the procedure described by Najera et al (J. Chem. Soc., Perkin Trans. I (1988) 1029–1032) and in EP-A-0644176. The following reaction scheme applies:

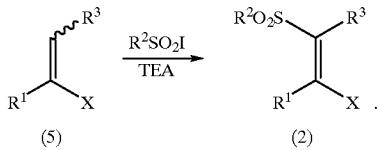

A compound of formula (5) where $R^1$ and $R^3$ are defined as for formula (2) is reacted with sulfonyl iodide of formula $R^2SO_2I$ where $R^2$ defined as for formula (2), in a solvent such as DCM, and then the reaction mixture is treated with a base such as triethylamine to eliminate hydrogen iodide and yield a vinyl sulfone of formula (2). When X is electron-withdrawing, e.g. $CO_2H$, and $R^3$ is H, the reaction is stereoselective and the stereochemistry of the resultant vinyl sulfones is E (trans) (Najera et al, supra). Formation of a single geometric isomer, rather than an E/Z mixture, facilitates straightforward purification by crystallisation.

The sulfonyl iodide may be prepared from the respective sodium sulfinic acid sodium salt ($R^2SO_2Na$) by shaking an aqueous solution of the latter with a solution of iodine in dichloromethane (DCM). Using this procedure, the sulfonyl iodide is extracted cleanly into the DCM layer which is subsequently dried and used immediately in the above reaction.

The following Examples 6 to 10 illustrate the invention. Examples 1 to 5 illustrate the preparation of vinyl sulfones (2) used as starting materials.

EXAMPLE 1

(E)-3-(4-Methoxybenzenesulfonyl)-2-propylacrylic acid

Sodium 4-methoxyphenylsulfinate (10.0 g, 51.49 mmol) was dissolved in water (50 ml). This solution was shaken with iodine (8.7 g, 34.29 mmol) in dichloromethane (60 ml). The dichloromethane layer turned from deep pink to orange. The dichloromethane layer was dried over magnesium sulfate and filtered into a flask containing 2-propylacrylic acid (2.0 g, 17.52 mmol). The solution was stirred overnight at room temperature and then cooled to 0° C. Triethylamine (7.3 ml, 51.49 mmol) was added and the solution was allowed to warm to room temperature over 2 hours. Sulphuric acid (2M, 50 ml) was added to quench the reaction. The organic phase was washed with 10% aqueous sodium bisulphite (50 ml), then extracted with sodium hydroxide (1 g) in water (50 ml). The aqueous layer was washed with MTBE (20 ml) and the acidifed with sulphuric acid (2M, 10 ml). The product was extracted into dichloromethane (2×30 ml) and the combined organic layers were washed with brine (20 ml), dried over magnesium sulfate, filtered and evaporated to give the title compound in 90% yield. This yellow solid was recrystallised from hot solvent (ethyl acetate:heptane:glacial acetic acid 1:1:0.2) to give the title compound as white crystals (4.02 g, 80%).

$^1$H NMR (200 MHz, $CDCl_3$): δ 1.0 (3H, t), 1.5 (2H, m), 2.8 (2H, dd), 3.7 (1H, bs), 3.95 (3H, s), 7.0 (2H, d), 7.25 (1H, s), 7.9 (2H, d).

$^{13}$C NMR (200 MHz, $CDCl_3$): δ 13.96, 22.44, 28.45, 55.70, 114.71, 129.95, 131.62, 138.91, 143.43, 164.11, 170.45.

EXAMPLE 2

(E)-3-(Toluene-4-sulfonyl)-2-propylacrylic acid

2-Propylacrylic acid (5.0 g, 43.80 mmol) was added to a solution of toluene-4-sulfonyl iodide (14.32 g, 65.70 mmol) in dichloromethane (100 ml). The solution was stirred overnight at room temperature and then cooled to 0° C. Triethylamine (12.2 ml, 87.6 mmol) was added and the solution was stirred for 1 hour then allowed to warm to room temperature over 2 hours. The organic solution was washed with water (100 ml), 1N hydrochloric acid ((100 ml) 10% aqueous sodium bisulfite (50 ml), then extracted with sodium hydroxide (5 g) in water (100 ml). The aqueous layer was washed with ethyl acetate (20 ml) and then acidifed with conc. sulfuric acid (3 ml). The product was extracted into ethyl acetate (2×50 ml) and the combined organic layers were washed with brine (20 ml), dried over magnesium sulfate, filtered and evaporated to give the title compound in 85% yield. This yellow solid was dissolved in methanol (100 ml) and stirred with activated charcoal (1 g). Filtration and evaporation gave a pale yellow solid which was slurried in dichloromethane:heptane 20:80. Filtration gave the title compound as white crystals (8.3 g, 70%).

$^1$H NMR (400 MHz, $CDCl_3$): 67 1.0 (3H, t), 1.5 (2H, m), 2.5 (3H, 3), 2.8 (2H, dd), 7.25 (1H, s), 7.4 (2H, d), 7.85 (2H, d).

EXAMPLE 3

(E)-3-Benzenesulfonyl-2-propylacrylic acid

Sodium benzenesulfinate (11.21 g, 68.27 mmol) was dissolved in water (100 ml). This solution was shaken with iodine (17.33 g, 68.27 mmol) in dichloromethane (100 ml).

The dichloromethane layer turned from deep pink to orange. The dichloromethane layer was dried over magnesium sulphate and filtered into a flask containing methy 2-propylacrylate (5.0 g, 39.01 mmol). The solution was stired overnight at room temperature and then cooled to 0° C. Triethylamine (11 ml, 78.01 mmol) was added and the solution was allowed to warm to room temperature over 2 hours. The mixture was diluted with water and the organic layer was washed with 1N hydrochloric acid (75 ml), 10% aqueous sodium bisulfite (75 ml), and brine, then dried over magnesium sulfate, filtered and evaporated to give (E)-3-benzenesulfonyl-2-propylacrylic acid methyl ester (9.1 g, 87% yield).

$^1$H NMR (200 MHZ, CDCl$_3$): δ 0.95 (3H, t), 1.5 (2H, m), 2.85 (2H, dd), 3.8 (3H, 3), 7.25 (1H, s), 7.65 (5H, m), 7.95 (2H, m).

(E)-3-benzenesulfonyl-2-propylacrylic acid methyl ester (5.0 g, 16.84 mmol) was dissolved in THF/water 3:1 (20 ml). Lithium hydroxide (0.86 g, 20.49 mmol) was added and the solution was stirred at room temperature overnight. The solvent was evaporated and the mixture was partitioned between ethyl acetate (50 ml) and water (40 ml). The aqueous layer was acidifed with 2M H$_2$SO$_4$ (6 ml) and the product was extracted into ethyl acetate (2×30 ml). The combined organic layers were washed with 2M H$_2$SO$_4$ (20 ml), brine, dried over magnesium sulfate, filtered and evaporated to give the title compound in 83% yield.

$^1$H NMR (400 MHz, CDCl$_3$): 67 1.0 (3H, t), 1.55 (2H, m), 2.8 (2H, dd), 3.5 (3H, 3), 6.95 (1h, bs), 7.25 (1H, s), 7.6 (3H, m), 7.7 (2H, m), 7.95 (2H, m).

EXAMPLE 4

(E)-2-Propyl-3-[4-(pyridine-4-carbonyl) benzenesulfonyl]acrylic acid

Sodium 4-(pyridine-4-carbonyl)benzenesulfinate (3.33 g, 14.04 mmol) was dissolved in water (60 ml). This solution was shaken with iodine (3.56 g, 34.29 mmol) in dishloromethane (40 ml). The dichloromethane layer turned from deep pink to orange. The dishloromethane layer was dried over magnesium sulfate and filtered into a flask containing 2-propylacrylic acid (0.8 g, 7.02 mmol). The solution was stirred overnight at room temperature and then cooled to 0° C. Triethylamine (4.0 ml, 28.08 mmol) was added and the solution was allowed to warm to room temperature over 2 hours. The mixture was acidified to pH 4 by addition of 10% citric acid. The layers were separated and the product was extracted with 2M sodium hydroxide (3×50 ml). The combined aqueous phase was washed with ethyl acetate (50 ml), the acidified to pH 4 with citric acid. The product was extracted into ethyl acetate (2×50 ml), then back into 1M hydrochloric acid (100 ml). The aqueous layer was washed with ethyl acetate (2×50 ml), then solid sodium hydrogen carbonate was added to pH 4. The product was extracted into dichloromethane (2×50 ml) and the combined organic layers were washed with brine (20 ml), dried over magnesium sulfate, filtered and evaporated to give the title compound (0.60 g, 24%).

$^1$H NMR (200 MHz. DMSO): 67 0.9 (3H, t), 1.45 (2H, m), 2.75 (2H, dd) 7.3 (1H, s), 7.7 (2H, m), 8.05 ( 2H, m), 8.2 ( 2H, m), 8.85 (2H, m).

EXAMPLE 5

(E)-3-(Methoxybenzenesulfonyl)-2-[(3,4,4-trimethyl-2,5-dioxoimidazolidin-1-yl)propyl]acrylic acid Sodium 4-methoxyphenylsulfinate (10.0 g, 51.49 mmol) was dissolved in water (100 ml). This solution was shaken with iodine (9.8 g, 36.61 mmol) in dichloromethane (100 ml). The dichloromethane layer turned from deep pink to orange. The dichloromethane layer was dried over magnesium sulfate and filtered into a flask containing sodium 2-carboxy-5-(3,4,4-trimethyl-2,5-dioxoimidazolidin-1-yl) pent-1-ene-1-sulfinate (6.47 g, 25.74 mmol). The solution was stirred overnight at room temperature and then cooled to 0° C. Triethylamine (11.0 ml, 77.23 mmol) was added and the solution was allowed to warm to room temperature over 2 hours. Sulfuric acid (2M, 50 ml) was added to quench the reaction. The organic phase was washed with 10% aqueous sodium bisulfite (50 ml), then extracted with sodium hydroxide (2M, 3×50 ml). The aqueous layer was washed with dichloromethane (50 ml) and the acidifed with sulfuric acid (2M) to pH 1. The product was extracted into dichloromethane (3×50 ml) and the combined organic layers were washed with brine (20 ml), dried over magnesium sulfate, filtered and evaporaed to give the title compound in 88% yield. This yellow oil was crystallised from MTBE/DCM 40:1 to give the title compound as a white solid (5.6 g, 51%).

$^1$H NMR (200 MHz, CDCl$_3$): δ 1.45 (6H, s), 1.7 (2H, m), 2.85 (2H, m), 2.97 (3H, s), 3.5 (1H, bs), 3.6 (2H, t), 3.9 (3H, s), 7.05 (2H, d), 7.2 (1H, s), 7.85 (2H, d).

EXAMPLE 6

2-(4-Methoxybenzenesulfonylmethyl)pentanoic acid (E)-3-(4-Methoxybenzenesulfonyl)-2-propylacrylic acid (1.0 g, 3.52 mmol) was dissolved in degassed methanol (15 ml) and [(S,S)-MeDuPHOS Rh (COD)]BF$_4$ (22 mg, 3.52× 10$^{-2}$ mmol) was added under a stream of nitrogen. This solution was injected into the pressure vessel under nitrogen, and then the bomb was charged with hydrogen. The mixture was hydrogenated at 1035 kPa (150 psi) for 2 hour at room temperature. The methanol was removed under reduced pressure to give the title compound (1.0 g, 99% yield). E.e. was determined by chiral HPLC to be 96% [Chirocel OD; 20% IPA-80% heptane; 1 ml/min; 254 nm; major enantiomer Rf 10.91 min., minor enantiomer Rf 9.71 min.]

$^1$H NMR (200 MHz, CDCl$_3$): 67 0.9 (3H, t), 1.35 (2H, m), 1.65 (2H, m), 2.9 (1H, m), 3.1 (1H, m), 3.65 (1H, m), 3.9 (3H, s), 7.0 (2H, d), 7.85 (2H, d).

EXAMPLE 7

2-Benzenesulfonylmethylpentanoic acid (E)-2-Propyl-3-phenylsulfonylacrylic acid (0.3 g, 1.18 mmol) was dissolved in degassed methanol (15 ml) and [(S,S)-EtDuPHOS Rh (COD)]BF$_4$ (8 mg, 1.18×10$^{-2}$ mmol) was added under a stream of nitrogen. This solution was injected into the pressure vessel under nitrogen, and then the bomb was charged with hydrogen. The mixture was hydrogenated at 2070 kPa (300 psi) for 3 hour at room temperature. The methanol was removed under reduced pressure to give the title compound (0.31 g, 100% yield). E.e. was determined by chiral HPLC to be 92% e.e. [Chiropak AD; 5% ethanol-95% heptane; 1 ml/min; 254 nm; major enantiomer Rf 18.46 min., minor enantiomer Rf 15.22 min.]

$^1$H NMR (200 MHz, CDCl$_3$): 67 0.9 (3H, t), 1.3 (2H, m), 1.65 (2H, m), 2.95 (1H, m), 3.15 (1H, m), 3.7 (1H, m), 7.65 (3H, m), 8.0 (2H, d).

EXAMPLE 8

2-(Toluene-4-sulfonylmethyl)pentanoic acid (E)-2-Propyl-3-p-tolyslfonylacrylic acid (0.3 g, 1.11 mmol) was dissolved in degassed methanol (15 ml) and

[(S,S)-EtDuPHOS Rh (COD)]BF$_4$ (7 mg, 1.11×10$^{-2}$ mmol) was added under a stream of nitrogen. This solution was injected into the pressure vessel under nitrogen, and then the bomb was charged with hydrogen. The mixture was hydrogenated at 2070 kPa (300 psi) for 3 hour at room temperature. The methanol was removed under reduced pressure to give the title compound (0.29 g, 99% yield). E.e. was determined by chiral HPLC to be 97% e.e. [Chirocel OD; 10% IPA-90% heptane; 1 ml/min; 254 nm; major enantiomer Rf 12.87 min, minor enantiomer Rf 11.12 min.]

$^1$H NMR (200 MHz, CDCl$_3$): δ 0.9 (3H, t), 1.3 (2H, m), 1.65 (2H, m), 2.45 (3H, s), 2.9 (1H, m), 3.15 (1H, m), 3.65 (1H, m), 7.4 (3H, m), 7.8 ( 2H, d).

EXAMPLE 9

2-[4-(Pyridine-4-carbonyl)benzenesulfonylmethyl] pentanoic acid (E)-2-Propyl-3-[4-(pyridine-4-carbonyl)benzenesulfonyl] acrylic acid was converted into its HBF$_4$ salt on treatment with 1 equivalent of HBF$_4$ in DCM and evaporation to dryness. (E)-2-Propyl-3-[4-(pyridine-4-carbonyl) benzenesulfonyl]-acrylic acid hydrofluoroborate (0.22 g, 0.49 mmol) and [(R,R)-MeDuPHOS Rh (COD)]BF$_4$ (6 mg, 0.49×10$^{-2}$ mmol) were place in the pressure vessel under nitrogen, and then the bomb was degassed with hydrogen. Degassed methanol (10 ml) was added and the mixture was hydrogenated at 2070 kPa (300 psi) hydrogen for 16 hour at room temperature. The methanol was removed under reduced pressure. The product was treated with aqueous sodium bicarbonate and then citric acid was added until pH 4. The product was extracted into dichloromethane, which was dried over magnesium sulfate and then evaporated to give the title compound (0.15 g, 83% yield). E.e. was determined by chiral HPLC to be 96% e.e.

$^1$H NMR (200 MHz, DMSO): 67 0.9 (3H, t), 1.45 (2H, m), 1.7 (2H, m) 3.0 (2H, bs+m), 3.25 (1H, dd), 3.8 (1H, dd), 7.6 (2H, m), 7.9 (2H, m), 8.05 (2H, m), 8.8 (2H, m), 8.85 (2H, m).

EXAMPLE 10

3-(4-Methoxybenzenesulfonyl)-2-[3,4,4-trimethyl-2, 5-dioxoimidazolidin-1-yl-propyl]acrylic acid E-3-(Methoxybenzenesulfonyl)-2-[(3,4,4-trimethyl-2,5-dioxoimidazolidin-1-yl)-propyl]acrylic acid (1.0 g, 2.36 mmol) and [(R,R)-MeDuPHOS Rh (COD)]BF$_4$ (14 mg, 2.36×10$^{-2}$ mmol) were place in the pressue vessel under nitrogen, and then the bomb was degassed with hydrogen. Degassed methanol (10 ml) was added and the mixture was hydrogenated at 2070 kPa (300 psi) hydrogen for 3 hour at room temperature. The methanol was removed under reduced pressure to give the title compound (1.00 g, 99% yield). E.e. was determined by chiral HPLC to be >97% e.e. [Chirocel AD; 45% IPA/55% heptane/0.1% TFA; 1 ml/min; 215 nm; major enantiomer Rf 8.7 min, minor enantiomer Rf 11.9 min.]

What is claimed is:

1. A process for the preparation of an enantioenriched sulfone of formula (1), comprising asymmetric hydrogenation of a vinyl sulfone of formula (2)

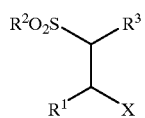

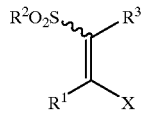

in the presence of a stereoselective chiral catalyst, wherein R$^1$, R$^2$, and R$^3$ are each independently a hydrocarbon group of less than 20 carbon atoms, optionally substituted at any position, or either of R$^1$ and R$^3$ is H, and X is a coordinating group selected from the group consisting of CO$_2$H or a salt form thereof, CO$_2$R, CONHOH, CONH$_2$, CONHR, and CONR$_2$ and each R is independently a hydrocarbon substituent of up to 20 carbon atoms.

2. The process, according to claim 1, wherein said chiral catalyst is a complex of a transition metal and a chiral ligand.

3. The process, according to claim 2, wherein said transition metal is selected from the group consisting of rhodium, ruthenium, and iridium.

4. The process, according to claim 3, wherein said transition metal is rhodium.

5. The process, according to claim 2, wherein said chiral ligand is selected from the group consisting of a monophosphine and a diphosphine.

6. The process, according to claim 5, wherein said phosphine is cyclic.

7. The process, according to claim 1, wherein R$^1$ is selected from the group consisting of alkyl and arylalkyl, R$^2$ is aryl, R$^3$ is H, and X is CO$_2$H.

8. The process, according to claim 1, wherein said vinyl sulfone is a single geometric isomer, wherein said R$^2$SO$_2$ and X groups are trans.

9. The process, according to claim 1, wherein said vinyl sulfone substrate is an E/Z mixture of geometric isomers.

10. The process, according to claim 1, wherein said R$^1$ is an optionally-substituted hydrocarbon group.

11. The process, according to claim 1, which additionally comprises converting the group X to give an enantiopure compound having therapeutic utility as an inhibitor of matrix metalloproteinases.

12. The process, according to claim 6, wherein said phosphine incorporates a trans-2,5-disubstituted phospholane moiety of formula (4)

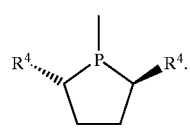

or the opposite enantiomer thereof, wherein R$^4$ is a hydrocarbon substituent of up to 20 carbon atoms.

13. The process, according to claim 12, wherein said R$^4$ is C$_{1-10}$ linear or branched alkyl.

14. The process, according to claim 13, wherein said phosphine is MeDuPHOS or EtDuPHOS.

* * * * *